(12) United States Patent
Vena et al.

(10) Patent No.: US 10,716,506 B2
(45) Date of Patent: Jul. 21, 2020

(54) PROSTHETIC IMPLANT AND METHOD FOR THE PRODUCTION OF SUCH AN IMPLANT

(71) Applicants: CENTRE NATIONAL DE LA RECHERCHE SCIENTIFIQUE, Paris (FR); UNIVERSITE DE MONTPELLIER, Montpellier (FR); BONETAG, Perpignan (FR)

(72) Inventors: Arnaud Vena, Saint Mathieu de Tréviers (FR); Brice Sorli, Montagnac (FR); Stéphan Cahuzac, Villeveyrac (FR); Stéphane Naudi, Perpignan (FR)

(73) Assignees: CENTRE NATIONAL DE LA RECHERCHE SCIENTIFIQUE, Paris (FR); UNIVERSITE DE MONTPELLIER, Montpellier (FR); BONETAG, Perpignan (FR)

( * ) Notice: Subject to any disclaimer, the term of this patent is extended or adjusted under 35 U.S.C. 154(b) by 0 days.

(21) Appl. No.: 16/318,665

(22) PCT Filed: Jul. 20, 2017

(86) PCT No.: PCT/EP2017/068422
§ 371 (c)(1),
(2) Date: Jan. 17, 2019

(87) PCT Pub. No.: WO2018/015513
PCT Pub. Date: Jan. 25, 2018

(65) Prior Publication Data
US 2019/0239804 A1  Aug. 8, 2019

(30) Foreign Application Priority Data
Jul. 20, 2016 (FR) ..................... 16 56918

(51) Int. Cl.
*A61B 5/00* (2006.01)
*A61F 2/30* (2006.01)
(Continued)

(52) U.S. Cl.
CPC .......... *A61B 5/4851* (2013.01); *A61B 5/0031* (2013.01); *A61B 5/076* (2013.01);
(Continued)

(58) Field of Classification Search
CPC .... A61F 2/38; A61F 2/389; A61F 2002/3067; A61F 2002/4666; A61F 2250/0002;
(Continued)

(56) References Cited

U.S. PATENT DOCUMENTS 7,333,013 B2 * 2/2008 Berger .................. A61B 90/90
                                                                  235/375
7,384,403 B2 * 6/2008 Sherman .............. A61B 5/0002
                                                                  600/587

(Continued)

FOREIGN PATENT DOCUMENTS

WO  2015/024821 A1  2/2015

OTHER PUBLICATIONS

French Search Report from French Patent Application No. 1656918, dated Mar. 20, 2017.
(Continued)

*Primary Examiner* — David H Willse
*Assistant Examiner* — Javier G Blanco
(74) *Attorney, Agent, or Firm* — Greer, Burns & Crain, Ltd.

(57) ABSTRACT

A prosthetic implant includes a cavity that opens at an outer face of the prosthetic implant, the cavity forming a housing for receiving: a printed circuit including a radio tag; and a cover which closes the cavity at least partially when posi-
(Continued)

tioned on the implant in a so-called closed position, the radio tag and printed circuit being removably housed in the cavity.

14 Claims, 1 Drawing Sheet

(51) Int. Cl.
  *A61F 2/38* (2006.01)
  *A61B 5/07* (2006.01)
  *A61F 2/46* (2006.01)
  *A61B 5/103* (2006.01)
(52) U.S. Cl.
  CPC ............ *A61B 5/4528* (2013.01); *A61B 5/686* (2013.01); *A61F 2/30* (2013.01); *A61F 2/38* (2013.01); *A61B 5/103* (2013.01); *A61B 5/1036* (2013.01); *A61B 2560/045* (2013.01); *A61B 2562/0252* (2013.01); *A61B 2562/0257* (2013.01); *A61F 2/389* (2013.01); *A61F 2002/3067* (2013.01); *A61F 2002/3071* (2013.01); *A61F 2002/30087* (2013.01); *A61F 2002/30957* (2013.01); *A61F 2002/4666* (2013.01); *A61F 2250/0002* (2013.01); *A61F 2250/0096* (2013.01)
(58) Field of Classification Search
  CPC ........... A61F 2250/0096; A61B 5/0031; A61B 5/103; A61B 5/686; A61B 5/4851; A61B 5/1036; A61B 5/0002; A61B 5/4528
  See application file for complete search history.

(56) References Cited

U.S. PATENT DOCUMENTS

| | | | |
|---|---|---|---|
| 7,575,602 B2* | 8/2009 | Amirouche | A61B 5/0031 623/18.11 |
| 2003/0069644 A1* | 4/2003 | Kovacevic | A61F 2/389 623/20.32 |
| 2005/0010299 A1* | 1/2005 | Disilvestro | A61B 5/076 623/18.12 |
| 2006/0047283 A1 | 3/2006 | Evans, III et al. | |
| 2011/0319755 A1* | 12/2011 | Stein | A61B 5/0031 600/437 |
| 2013/0023794 A1* | 1/2013 | Stein | G06Q 50/24 600/587 |
| 2013/0079668 A1* | 3/2013 | Stein | A61B 5/686 600/587 |
| 2015/0238691 A1 | 8/2015 | Boyden et al. | |

OTHER PUBLICATIONS

International Search Report from International Patent Application No. PCT/EP2017/068422, dated Sep. 7, 2017.
Written Opinion of the International Searching Authority from International Patent Application No. PCT/EP2017/068422, dated Sep. 7, 2017.

* cited by examiner

PROSTHETIC IMPLANT AND METHOD FOR THE PRODUCTION OF SUCH AN IMPLANT

BACKGROUND

The invention relates to the field of prostheses, preferably that of joint prostheses, also called prosthetic implants, for example for the hip, knee, spine or elbow, which are artificial devices intended to compensate for an organ or a limb, or to replace it.

The invention relates in particular to the field of prostheses equipped with a communication means.

Prostheses including an RFID tag connected to physical quantity sensors, for example temperature sensors, are known. Such prostheses make it possible, for example, to monitor the temperature over time.

The RFID tag is permanently installed in contact with the prosthesis, which leads to various drawbacks. Replacing faulty RFID tags can be a problem. Implanting the prosthesis without damaging the RFID tag, which is fragile, is a problem.

A purpose of the invention is to propose a prosthetic implant:
  replacement of the RFID tag of which is easier than replacement of the RFID tag in a prosthetic implant according to the prior art, and/or
  the RFID tag of which is not damaged during implantation of the prosthesis.

SUMMARY

According to a first aspect of the invention, an above-mentioned objective is reached with a prosthetic implant comprising a cavity that opens onto an outer face of the prosthetic implant, the cavity forming a housing for receiving:
  a printed circuit board including an RFID tag, the RFID tag comprising an antenna connected to an electronic chip containing an identifier and additional data,
  a cover (cap) closing at least in part the cavity when it is positioned over the implant in a position called closed position.
According to the first aspect of the invention, the cover and the printed circuit board are received removably in the cavity.

The printed circuit board, also called PCB, can comprise a support of the dielectric type, also called a substrate. The printed circuit board can be arranged, in the closed position of the cover, within the cavity.

The support can be bordered by the antenna on one, or more, of its faces.

Additional data can originate from recordings produced from data captured by physical variable sensors. The physical variable sensors can for example be force or temperature sensors.

Replacement of the RFID tag is preferably easier than replacement of the RFID tag in a prosthetic implant according to the prior art.

The RFID tag is preferably not damaged during implantation of the prosthetic implant.

Preferably, the cover forms a boundary between the cavity, which is inside the implant, and a part outside the implant.

The cover can advantageously completely close the cavity.

Communication with the RFID tag can be carried out using the protocol defined by the standard "EPC Gen 2" in the UHF band (standard ISO/IEC 18000-6c). This protocol allows the reading/writing of data.

In the HF band, the standards used are ISO/IEC 14443 and ISO/IEC 15693.

Communication can be two-way.

Advantageously, the prosthetic implant can comprise a capacitive proximity sensor that can be arranged on the printed circuit board and can be connected to the printed circuit board. The detection principle can preferably be based on a dielectric measurement of the biological tissues close to the cover. A loosening can be detected if a relative variation in the dielectric properties (difference in the dielectric constant between the bone, cement, body fluid) is detected.

According to a possibility, the cover can have a region separating the cavity from the outside of the prosthetic implant, said region being capable of being designed to transmit a force exerted from an outer side of said region to an inner side of said region.

The region can be produced in a single piece with the cover, the thickness being reduced at the level of, preferably over the entire surface of, said region.

Preferably, the cover has a window arranged on a surface separating the cavity from the outside of the prosthetic implant, the window being arranged in order to receive a deformable membrane, the deformable membrane being arranged in order to transmit a force exerted on the membrane to a force sensor arranged on the printed circuit board and connected to the printed circuit board. The cover can be thinned in order to promote the deformations of the membrane.

The force sensor can be of the piezoresistive type and a force-transmission element can be functionally arranged between the membrane and the force sensor, the transmission element capable of being arranged in order to transmit a force exerted on said membrane to the force sensor. The resistance of a piezoresistive material can vary depending on mechanical strains.

The force-transmission element can be a deformable body, a movable part, a spring, a metal strip.

The force sensor can be of the capacitive type and a reaction element can be arranged between the membrane and the force sensor, the reaction element can be firmly fastened to the membrane, on the side of a face of the membrane turned towards the cavity, the reaction element capable of being arranged in order to be displaced when a force is exerted on said membrane.

The reaction element can be a metal insert. The reaction element can be clipped or bonded to the membrane. The reaction element and electrodes of the force sensor of the capacitive type form a capacitance. This capacitance can make it possible to detect a deformation of the membrane. The capacitance can vary when the reaction element is displaced.

The reaction element can be a high-permittivity dielectric insert, for example made of ceramic.

Advantageously, the force sensor can be of the piezoelectric type and a flexible piezoelectric body can be arranged between the membrane and the force sensor; the flexible body can be firmly fastened to the membrane, on the side of a face of the membrane turned towards the cavity, the flexible body capable of being arranged in order to be deformed when a force is exerted on said membrane.

The flexible body can be bonded to the deformable membrane. Deformation of the membrane can induce a mechanical deformation of the piezoelectric material and can produce electrical charges.

Preferably, the antenna can be arranged on the printed circuit board on the side of the outer face of the prosthetic implant when the printed circuit board is received in the cavity. Preferably, the radiation may not be confined in the cavity. The radiation can be propagated outside of the prosthetic implant.

Preferably, at least one face of the antenna is arranged opposite a face of the metal implant. Preferably, the face of the antenna arranged opposite the face of the metal implant is at a distance below a threshold, called coupling threshold. Said coupling threshold is determined in order to allow coupling between said face of the antenna and said face of the metal implant when the antenna is positioned in the housing.

The printed circuit board can be firmly fastened to the cover. The printed circuit board can for example be fixed to the cover, for example by means of pins arranged between the printed circuit board and the cover. The cover can for example be moulded over the printed circuit board. The mechanical strength of the implant over time and/or the resistance to impacts during fitting of the implant can, for example, thus be improved.

The printed circuit board can be mounted removably with respect to the cover. A resin can be injected into the cover in order to hold the printed circuit board on the cover. Such a resin, once solidified, can produce a piezoresistive material.

The cover can be designed in order to receive a sliding drawer having a housing for receiving the printed circuit board.

The cover can have a biocompatible material over all or part of the exposed surface of the cover when the cover is positioned in the closed position.

The biocompatible material can be polyethylene PE, PEEK, polypropylene PP, polysulphone PS, PTFE. Polyethylene PE is used in prostheses. Another biocompatible material can be Parylene.

The cover can be held in a closed position by a resin injected over at least a portion of said cover, in particular at the boundary formed by the cover and the outer surface onto which the cavity opens. The resin makes it possible to ensure the sealing of the cavity when the cover is in the closed position. The RFID tag is thus more protected. In particular, the resin can be biocompatible. The standard of the resin can be the standard USP Class VI or standard ISO 10993-5.

The cavity can be a groove arranged in order to co-operate with the cover.

The cavity and the cover can form a dovetail. The groove can be formed by the cavity. The tenon can be formed by the cover.

The implant according to the invention can comprise a support arranged in the cavity provided to receive the printed circuit board and to form with the cover a sealed compartment. The RFID tag is thus more protected.

The support can have a thickness at least less than half the thickness of the cavity.

The support can comprise a housing having the shape of the printed circuit board.

The support can be made of a biocompatible material, in particular an impervious material, for example metals and metal alloys such as titanium, 316L stainless steel.

The support can be made of polymer, metal or ceramic such as zirconia.

Advantageously, at least one face of the antenna can be arranged opposite at least one face of the prosthetic implant, said face of the prosthetic implant being made of metal, so as to produce an inductive and/or capacitive coupling between said at least one face of the antenna and said at least one face of the prosthetic implant, preferably at a distance less than 2 mm. The prosthetic implant can be made entirely of metal. Thus, the natural radiation capacity of the prosthetic implant is used to amplify the radiation of the antenna.

According to another aspect of the invention, a method for the production of a prosthetic implant according to the first aspect of the invention is proposed.

The production method can comprise production of a solid prosthesis and a step of machining the solid prosthesis in order to form the cavity of the prosthetic implant.

Alternatively, or in addition to the above, the production method can be carried out directly from a mould.

BRIEF DESCRIPTION OF THE DRAWINGS

Other features and advantages of the invention will become apparent on reading the detailed description of embodiments which are in no way limitative, with respect to the attached drawings in which.

DETAILED DESCRIPTION

As these embodiments are in no way limitative, variants of the invention can in particular be realised, comprising only a selection of the characteristics described hereinafter, as described or in general terms, in isolation from the other characteristics described, if this selection of characteristics is sufficient to confer a technical advantage or to differentiate the invention with respect to the state of the art.

Figure 1:
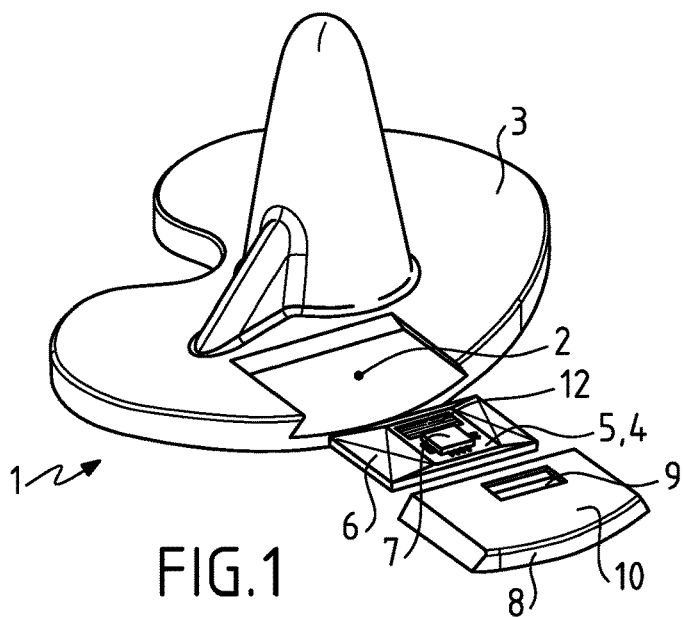
FIG. 1 is a perspective drawing of an embodiment of a prosthetic implant according to the invention.

FIG. 1 shows a prosthetic implant 1, preferably made of metal, according to the invention. The prosthetic implant 1 is a tibial plateau. The prosthetic implant 1 comprises a cavity 2 opening onto an outer face 3 of the prosthetic implant 1.

The method for the production of a prosthetic implant 1 can comprise a production of a solid prosthesis, preferably made of metal, and a step of machining the solid prosthesis in order to form the cavity 2 of the prosthetic implant 1.

Alternatively, or in addition to the above, the method for the production of the prosthetic implant 1 can be carried out directly from a prosthesis mould, preferably made of metal.

The cavity 2 forms a housing and can receive:
- a printed circuit board 4 including an RFID tag 5. The RFID tag 5 comprises an antenna 6 connected to an electronic chip 7 containing an identifier and additional data;
- a cover 8 closing at least in part the cavity when it is positioned on the implant (see FIG. 2) in a position called closed position.

In an embodiment, the cavity 2 represents 7.2% of the volume of the prosthetic implant. Of course, this ratio can vary depending on the size of the prosthetic implant.

Communication with the RFID tag 5 can be carried out using the protocol defined by the standard "EPC Gen 2" in the UHF band (standard ISO/IEC 18000-6c). This protocol allows the reading/writing of data.

In the HF band, the standards used are ISO/IEC 14443 and ISO/IEC 15693.

Communication can be two-way.

The cover 8 can protect the cavity 2.

The cover 8 can protect the printed circuit board 4 when then printed circuit board 4 is arranged in the cavity 2.

The cover 8 and the printed circuit board 4 are received removably in the cavity 2.

The cover 8 forms a boundary between the cavity 2 which is inside the prosthetic implant 1 and a part outside the implant.

The cover 8 can advantageously completely close the cavity 2, which is not shown by the figures.

The prosthetic implant can comprise a capacitive proximity sensor, but this is not shown by the figures. The capacitive sensor can be arranged on the printed circuit board and can be connected to the printed circuit board. The detection principle can be based on a dielectric measurement of the biological tissues close to the cover. A loosening can be detected if a relative variation in the dielectric properties (difference in the dielectric constant between the bone, cement, body fluid) is detected.

Figure 2:
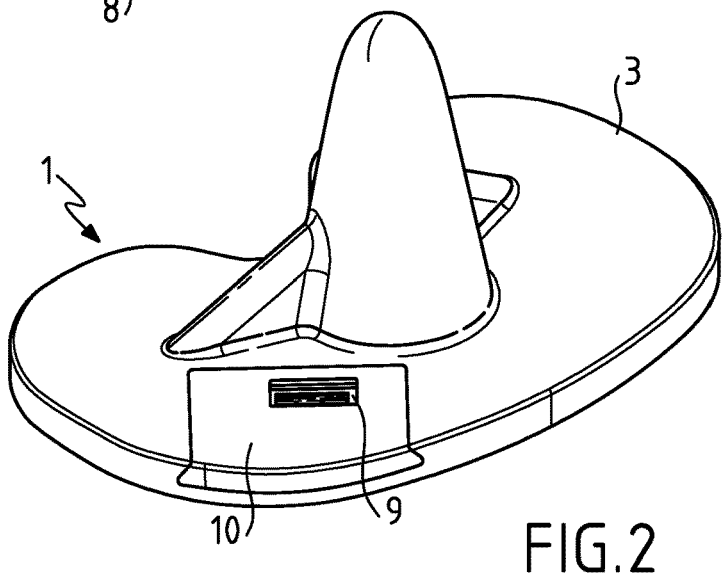
FIG. 2 is another perspective drawing of the embodiment of the prosthetic implant in FIG. 1.

As shown in FIGS. 1 and 2, the cover 8 has a window 9 arranged on a surface 10 separating the cavity from the outside of the prosthetic implant. The window 9 is arranged in order to receive a deformable membrane (not shown). The deformable membrane is arranged in order to transmit a force exerted on the membrane to a force sensor 12 arranged on the printed circuit board 4 and connected to the printed circuit board 4. The cover 8 can be thinned in order to promote the deformations of the membrane.

The force sensor 12 is of the piezoresistive type and a force-transmission element (not shown) is functionally arranged between the membrane and the force sensor 12. The transmission element is arranged in order to transmit a force exerted on the membrane to the force sensor 12.

The force-transmission element can be a deformable body. In other examples, the force-transmission element could be a movable part, a spring, or a metal strip.

In an example that is also not shown, alternatively or in addition to the above, the force sensor can be of the capacitive type and a reaction element (not shown) can be arranged between the membrane and the force sensor. The reaction element can be firmly fastened to the membrane, on a side of a face of the membrane turned towards the cavity 2. The reaction element can be arranged in order to be displaced when a force is exerted on said membrane.

In this example that is also not shown, alternatively or in addition to the above, the reaction element can be a metal insert (not shown). The reaction element can be clipped or bonded to the membrane. The reaction element and the electrodes of the force sensor of the capacitive type form a capacitance. This capacitance can make it possible to detect a deformation of the membrane. The capacitance can vary when the reaction element is displaced.

According to an alternative that is also not shown, alternatively or in addition to the above, the reaction element can be a high-permittivity dielectric insert (not shown), for example made of ceramic.

In an example that is also not shown, alternatively or in addition to the above, the force sensor 12 can be of the piezoelectric type and a flexible piezoelectric body (not shown) can be arranged between the membrane and the force sensor 12. The flexible body can be firmly fastened to the membrane on the side of a face (not shown) of the membrane turned towards the cavity 2. The flexible body can be arranged in order to be deformed when a force is exerted on the membrane.

The flexible body can be bonded to the deformable membrane. Deformation of the membrane can induce a mechanical deformation of the piezoelectric material and can produce electrical charges.

In the example shown in FIG. 1, the antenna 6 is arranged on the printed circuit board 4 on the side of the outer face 3 of the prosthetic implant 1 when the printed circuit board 4 is received in the cavity 2. The radiation of the antenna 6 may not be confined in the cavity. The radiation of the antenna 6 can be propagated outside the prosthetic implant 1.

In an example that is not shown, the printed circuit board 4 is firmly fastened to the cover 8. The printed circuit board 4 can for example be fixed to the cover 8, for example by means of pins arranged between the printed circuit board 4 and the cover 8. The cover 8 can for example be moulded over the printed circuit board 4.

In the example shown in FIG. 1, the printed circuit board 4 is mounted removably with respect to the cover 8. In this example, the cover 8 is designed in order to receive a sliding drawer (not shown) having a housing for receiving the printed circuit board 4.

The cover 8 can have a biocompatible material over all or part of the exposed surface of the cover 8 when the cover is positioned in the closed position. The biocompatible material can be polyethylene PE, PEEK, polypropylene PP, polysulphone PS, PTFE. In the example shown, the biocompatible material is polyethylene PE. The cavity can be a groove arranged in order to co-operate with the cover.

As shown in FIG. 1, the cavity 2 and the cover 8 form a dovetail. The groove of the dovetail is formed by the cavity 2. The tenon of the dovetail is formed by the cover 8.

Figure 3:
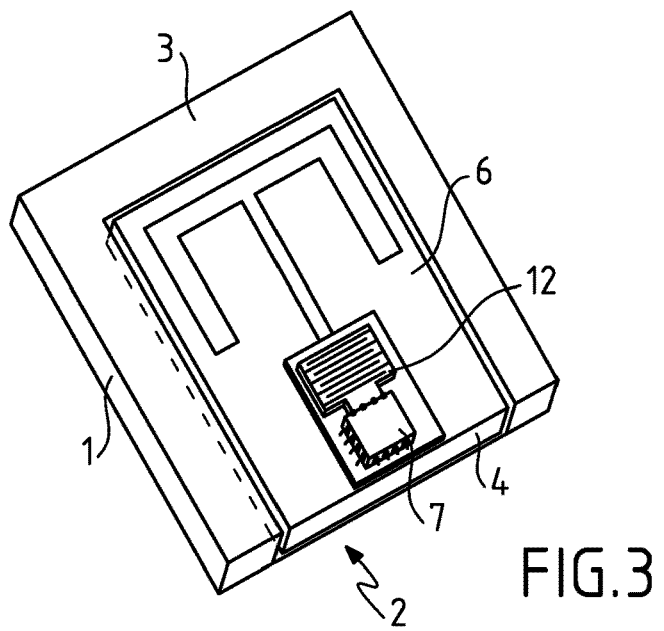
FIG. 3 is a perspective drawing of another embodiment of the prosthetic implant according to the invention.

With reference to FIG. 3 another embodiment of the implant according to the invention will now be described. The references used to describe FIG. 1 and FIG. 2 are used again.

FIG. 3 is a diagrammatic perspective view of the prosthetic implant 1 at the level of the cavity 2 adapted to receive the printed circuit board.

In this example, the housing has two open faces on the outside of the prosthetic implant, the other faces of the housing being constituted by faces of the prosthetic implant.

The printed circuit board can have a shape corresponding to the housing formed in the implant.

The circuit board support can for example be produced from an epoxy resin or a glass fibre-reinforced epoxy resin composite, for example of the FR-4 type, FR-4 ("Flame Resistant 4") being used for the production of the printed circuit board.

In particular, the printed circuit board can have a parallelepiped shape. The dimensions of the parallelepiped can be in a range of thicknesses from 0.1 to 5 mm, in a range of widths from 5 to 35 mm and in a range of lengths from 5 to 35 mm.

The printed circuit board support can be bordered by the antenna 6 over all or part of its faces opposite a face of the prosthetic implant. An inductive and capacitive coupling is thus formed between the prosthetic implant and the antenna.

For example, each distance between a first face of the antenna opposite the prosthetic implant and a second corresponding face of the prosthetic implant opposite said first face of the antenna can be less than 2 mm.

A smaller space makes it possible to promote the coupling of the surface currents of the antenna formed on the support of the printed circuit board with the metal prosthetic implant.

A metal prosthetic implant is a good conductor which allows the establishment of induced currents which are a source of electromagnetic radiation.

When induced currents are coupled between the antenna and the prosthetic implant, the intensity of the radiated field is significant.

It is also intended to arrange the faces of the printed circuit board that do not have conductive elements at a distance from the prosthetic implant, in order to improve the efficiency of the radiation through the openings.

In FIG. 3, the electronic chip 7 that comprises 16 pins is also shown.

Two pins are electrically connected to the antenna 6. Two other pins are electrically connected to the force sensor 12.

The face of the printed circuit board arranged on the side of the outer face 3 of the prosthetic implant has an opening in the shape of a T.

The sheath antenna can be made of copper. It can border the entirety of the printed circuit board except the two faces comprising openings.

Of course, the invention is not limited to the examples which have just been described and numerous adjustments can be made to these examples without exceeding the scope of the invention. In addition, the various characteristics, forms, variants and embodiments of the invention can be combined with one another in various combinations, provided that they are not incompatible or mutually exclusive.

The invention claimed is:

1. A prosthetic implant comprising:
   an upper surface, a lower bone-engaging surface, and a perimeter between said upper and lower surfaces,
   a cavity formed in said lower bone-engaging surface and opening onto an outer face of the perimeter of said prosthetic implant, said cavity forming a housing receiving:
     a printed circuit board including a radio-frequency identification (RFID) tag, said RFID tag comprising an antenna connected to an electronic chip containing an identifier and additional data;
     a force sensor arranged on the printed circuit board and connected to the printed circuit board; and
     a cover slidably received in said cavity, the cover closing at least in part said cavity when it is positioned on said implant in a position called closed position;
   wherein the RFID tag, force sensor, and the printed circuit board are removably housed in the cavity,
   wherein the cover has a window arranged on a surface separating the cavity from the outside of the prosthetic implant, said window being arranged in order to receive a deformable membrane and to transmit a force exerted on said membrane to said force sensor,
   wherein the cover comprises a shape and size complementary to shape and size of the cavity,
   wherein the cover is flush-mounted to the lower bone-engaging surface of the prosthetic implant when in said closed position, in which an exposed surface of said cover forms part of said lower bone-engaging surface,
   wherein the prosthetic implant is a tibial plate.

2. The prosthetic implant according to claim 1, comprising a capacitive proximity sensor arranged on the printed circuit board and connected to the printed circuit board.

3. The prosthetic implant according to claim 1, in which the window is produced in a single piece with the cover, a thickness of the cover being reduced at the level of said window.

4. The prosthetic implant according to claim 1, in which the force sensor is of the piezoresistive type and a force-transmission element is arranged between the membrane and said force sensor, the transmission element being arranged in order to transmit a force exerted on said membrane to the force sensor.

5. The prosthetic implant according to claim 1, in which the force sensor is of the capacitive type and a reaction element is arranged between the membrane and said force sensor, said reaction element being firmly fastened to the membrane on a face of the membrane turned towards the cavity, the reaction element being arranged in order to be displaced when a force is exerted on said membrane.

6. The prosthetic implant according to claim 1, in which the force sensor is of the piezoelectric type and a flexible piezoelectric body is arranged between the membrane and said force sensor, said flexible body being firmly fastened to the membrane on a face of the membrane turned towards the cavity, said flexible body being arranged in order to be deformed when a force is exerted on said membrane.

7. The prosthetic implant according to claim 1, in which the antenna is arranged on the printed circuit board and facing the lower bone-engaging surface of the prosthetic implant when the printed circuit board is housed in the cavity.

8. The prosthetic implant according to claim 7, in which the cover is arranged in order to receive a sliding drawer having a housing for receiving the printed circuit board.

9. The prosthetic implant according to claim 1, in which the printed circuit board is firmly fastened to the cover.

10. The prosthetic implant according to claim 1, in which the printed circuit board is mounted removably with respect to the cover.

11. The prosthetic implant according to claim 1, in which said cover has a biocompatible material over all or part of the exposed surface of said cover when the cover is positioned in the closed position.

12. The prosthetic implant according to claim 1, in which the cover is held in a closed position by a resin injected over at least a part of said cover.

13. The prosthetic implant according to claim 1, in which the cavity is a groove arranged in order to co-operate with the cover.

14. The prosthetic implant according to claim 1, in which the cavity and the cover form a dovetail.

* * * * *